US00PP30695P2

(12) United States Plant Patent
Oya et al.

(10) Patent No.: US PP30,695 P2
(45) Date of Patent: Jul. 9, 2019

(54) ***PETUNIA* PLANT NAMED 'MIYOPEGB60-1'**

(50) Latin Name: ***Petunia* X *hybrida***
Varietal Denomination: MIYOPEGB60-1

(71) Applicant: Seiichi Miyoshi, Tokyo (JP)

(72) Inventors: Hirotaka Oya, Shizuoka (JP); Genya Daido, Shizuoka (JP)

(73) Assignee: Seiichi Miyoshi, Tokyo (JP)

( * ) Notice: Subject to any disclaimer, the term of this patent is extended or adjusted under 35 U.S.C. 154(b) by 0 days.

(21) Appl. No.: 15/999,868

(22) Filed: Aug. 23, 2018

(51) Int. Cl.
*A01H 5/02* (2018.01)
*A01H 6/82* (2018.01)

(52) U.S. Cl.
USPC ..... Plt./356.1
CPC ..... *A01H 6/82* (2018.05); *A01H 5/02* (2013.01)

(58) Field of Classification Search
USPC ..... Plt./356.1
CPC ..... A01H 5/02
See application file for complete search history.

*Primary Examiner* — Kent L Bell
(74) *Attorney, Agent, or Firm* — C. A. Whealy

(57) ABSTRACT

A new and distinct *Petunia* plant named 'MIYOPEGB60-1', characterized by its upright to outwardly spreading and mounding plant habit; vigorous growth habit; freely branching habit; early and freely flowering habit; yellow-colored flowers; and good garden performance.

2 Drawing Sheets

Botanical designation: *Petunia* X *hybrida.*
Cultivar denomination: 'MIYOPEGB60-1'.

BACKGROUND OF THE INVENTION

The present invention relates to a new and distinct cultivar of *Petunia* plant, botanically known as *Petunia* X *hybrida* and hereinafter referred to by the name 'MIYOPEGB60-1'.

The new *Petunia* plant is a product of a planned breeding program conducted by the Inventors in Nagaizumicho, Shizuoka, Japan. The objective of the breeding program is to create new vigorous and freely-branching and uniformly mounding *Petunia* plants with yellow-colored flowers and good garden performance.

The new *Petunia* plant originated from a cross-pollination made by the Inventors in August, 2014 in Nagaizumicho, Shizuoka, Japan of an unnamed proprietary selection of *Petunia* X *hybrida*, not patented, as the female, or seed, parent with a proprietary selection of *Petunia* X *hybrida* identified as code number P26-349-1, not patented, as the male, or pollen, parent. The new *Petunia* plant was discovered and selected by the Inventors as a single flowering plant within the progeny of the stated cross-pollination in a controlled greenhouse environment in Nagaizumicho, Shizuoka, Japan in July, 2015.

Asexual reproduction of the new *Petunia* plant by in vitro meristem culture in a controlled greenhouse environment in Nagaizumicho, Shizuoka, Japan since April, 2016 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'MIYOPEGB60-1'. These characteristics in combination distinguish 'MIYOPEGB60-1' as a new and distinct *Petunia* plant:

1. Upright to outwardly spreading and mounding plant habit.
2. Vigorous growth habit.
3. Freely branching habit.
4. Early and freely flowering habit.
5. Yellow-colored flowers.
6. Good garden performance.

Plants of the new *Petunia* can be compared to plants of the female parent selection. In side-by-side comparisons, plants of the new *Petunia* differ primarily from plants of the female parent selection in flower color as flowers of plants of the new *Petunia* are darker and more intense yellow in color than flowers of plants of the female parent selection. In addition, flowers of plants of the new *Petunia* are more funnelform in shape than and not as salverform in shape as plants of the female parent selection.

Plants of the new *Petunia* can be compared to plants of the male parent selection. In side-by-side comparisons, plants of the new *Petunia* differ primarily from plants of the male parent selection in flower size as plants of the new *Petunia* have larger flowers than plants of the male parent selection.

Plants of the new *Petunia* can be compared to plants of 'Shockwave Yellow', not patented. In side-by-side comparisons, plants of the new *Petunia* differ primarily from plants of 'Shockwave Yellow' in the following characteristics:

1. Plants of the new *Petunia* are more vigorous than plants of 'Shockwave Yellow'.
2. Leaves of plants of the new *Petunia* are broader than leaves of plants of 'Shockwave Yellow'.

3. Flowers of plants of the new *Petunia* are darker and more intense yellow in color than flowers of plants of 'Shockwave Yellow'.

Plants of the new *Petunia* can also be compared to plants of 'Horizon Yellow', not patented. In side-by-side comparisons, plants of the new *Petunia* differ primarily from plants of 'Horizon Yellow' in the following characteristics:

1. Plants of the new *Petunia* are smaller than plants of 'Horizon Yellow'.
2. Plants of the new *Petunia* are more vigorous than plants of 'Horizon Yellow'.
3. Plants of the new *Petunia* have smaller flowers than plants of 'Horizon Yellow'.
4. Flowers of plants of the new *Petunia* are darker and more intense yellow in color than flowers of plants of 'Horizon Yellow'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph on the first sheet is a side perspective view of a typical flowering plant of 'MIYOPEGB60-1' grown in a container.

The photograph on the second sheet is a close-up view of a typical flower of 'MIYOPEGB60-1'.

DETAILED BOTANICAL DESCRIPTION

The aforementioned photographs and following observations and measurements describe plants grown during the spring and summer in 12-cm containers in a polyethylene-covered greenhouse in Fukuroishi, Shizuoka, Japan and under cultural practices typical of commercial *Petunia* production. During the production of the plants, day temperatures averaged 23° C., night temperatures averaged 10° C. and light levels averaged 80,000 lux. Plants were seven weeks from planting rooted cuttings when the photographs and description were taken. In the following description, color references are made to The Royal Horticultural Society Colour Chart, 2015 Edition, except where general terms of ordinary dictionary significance are used.

Botanical classification: *Petunia* X *hybrida* 'MIYOPEGB60-1'.

Parentage:

*Female, or seed, parent*.—Unnamed proprietary selection of *Petunia* X *hybrida*, not patented.

*Male, or pollen, parent*.—Proprietary selection of *Petunia* X *hybrida* identified as code number P26-349-1, not patented.

Propagation:

*Type*.—By in vitro meristem culture.

*Time to initiate roots, summer*.—About one week at soil temperatures about 20° C. and ambient temperatures ranging from 20° C. to 30° C.

*Time to initiate roots, winter*.—About one week at soil temperatures about 20° C. and ambient temperatures ranging from 10° C. to 20° C.

*Time to produce a rooted young plant, summer*.—About four weeks at soil temperatures about 20° C. and ambient temperatures ranging from 20° C. to 30° C.

*Time to produce a rooted young plant, winter*.—About five weeks at soil temperatures about 20° C. and ambient temperatures ranging from 10° C. to 20° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Upright to outwardly spreading and mounding plant habit; freely branching habit with about six primary lateral branches each with secondary lateral branches potentially developing at every node; dense and bushy appearance; pinching enhances development of lateral branches; vigorous growth habit; moderate growth rate.

*Plant height, soil level to top of foliar plane*.—About 5 cm.

*Plant height, soil level to top of floral plane*.—About 7 cm.

*Plant diameter* (*area of spread*).—About 20 cm.

*Lateral branches*.—Length: About 18 cm. Diameter: About 2 mm. Internode length: About 1.2 cm. Strength: Moderately strong. Aspect: Initially upright then outwardly spreading. Texture and luster: Densely pubescent; viscid; matte. Color, developing: Close to 144A. Color, developed: Close to 144A.

Leaf description:

*Arrangement*.—Alternate before flowering and after flowers develop; leaves simple.

*Length*.—About 4.3 cm.

*Width*.—About 2.5 cm.

*Shape*.—Ovate.

*Apex*.—Acute.

*Base*.—Attenuate.

*Margin*.—Entire.

*Texture and luster, upper and lower surfaces*.—Moderately pubescence; viscid; matte.

*Venation pattern*.—Pinnate, arcuate.

*Color*.—Developing leaves, upper surface: Close to 137B. Developing leaves, lower surface: Close to 138A. Fully expanded leaves, upper surface: Close to 137B; venation, close to 144A. Fully expanded leaves, lower surface: Close to 137B; venation, close to 137B.

*Petioles*.—Length: About 1 cm. Diameter: About 2 mm. Strength: Moderately strong. Texture and luster, upper and lower surfaces: Densely pubescence; viscid; matte. Color, upper and lower surfaces: Close to 144A.

Flower description:

*Flower type and flowering habit*.—Single axillary salverform flowers; flowers face upright to mostly outwardly; freely flowering habit with numerous flowers developing per plant during the flowering season.

*Natural flowering season*.—Long day responsive; long flowering period, plants flower from spring until the autumn, flowering continuous during this period; early flowering habit, plants begin flowering about six weeks after planting.

*Flower longevity on the plant*.—About ten days; flowers persistent.

*Fragrance*.—Slightly fragrant, pleasant.

*Flower buds*.—Length: About 3.5 cm. Diameter: Distally, about 7 mm; proximally, about 2 mm. Shape: Oblong, elongate. Texture and luster: Densely pubescent; viscid; matte. Color: Close to 144B.

*Flower diameter*.—About 4 cm.

*Flower depth* (*height*).—About 3.5 cm.

*Throat diameter, distal*.—About 1 cm.

*Tube length*.—About 1.5 cm.

*Tube diameter, proximally*.—About 5 mm.

*Petals*.—Quantity and arrangement: Five petals fused in a single whorl. Petal lobe length (from throat): About 1.5 cm. Petal lobe width: About 2 cm. Petal lobe shape: Obovate. Petal lobe apex: Cuspidate to emarginate. Petal lobe margin: Entire; slightly undulate. Petal lobe texture and luster, upper surface: Smooth, glabrous; matte. Petal lobe texture and luster, lower surface: Sparsely pubescent matte. Throat and tube texture and luster: Densely pubescent; viscid; matte. Color: When opening, upper surface: Close to 7A. When opening, lower surface: Close to 1A. Fully opened, upper surface: Close to 7A; venation, close to 7A; color does not change with development. Fully opened, lower surface: Close to 1C; venation, close to 144C; color does not change with development. Flower throat (inside): Close to 145A; venation, close to 145A. Flower tube (outside): Close to 145A; venation, close to 145A.

*Sepals*.—Quantity and arrangement: Five sepals fused in a single star-shaped whorl. Calyx length: About 1.2 cm. Calyx diameter: About 1 cm. Length: About 1.2 cm. Width: About 4 mm. Shape: Ligulate. Apex: Rounded, blunt. Margin: Entire. Texture and luster, upper and lower surfaces: Densely pubescent; viscid; matte. Color: When opening and fully opened, upper surface: Close to 137B. When opening and fully developed, lower surface: Close to 144A.

*Peduncles*.—Length: About 1.5 cm. Width: About 1 mm. Strength: Moderately strong. Angle: About 20° from the stem axis. Texture and luster: Densely pubescent; viscid; matte. Color: Close to 144A.

*Reproductive organs*.—Stamens: Quantity per flower: Five. Filament length: About 2 cm. Filament color: Close to 155A. Anther size: About 1.5 mm by 2 mm. Anther shape: Bi-lobed. Anther color: Close to 145B. Pollen amount: Moderate. Pollen color: Close to 155A. Pistils: Quantity per flower: One. Pistil length: About 2 cm. Style length: About 1.8 cm. Style color: Close to 145B. Stigma diameter: About 2 mm. Stigma shape: Capitate. Stigma color: Close to 143A. Ovary color: Close to 141C.

*Seeds and fruits*.—To date, seed and fruit development has not been observed on plants of the new *Petunia*.

Pathogen & pest resistance: To date, plants of the new *Petunia* have not been noted to be resistant to pathogens or pests common to *Petunia* plants.

Garden performance: Plants of the new *Petunia* have been observed to have good garden performance and have been observed to tolerate rain, wind and temperatures ranging from about 5° C. to about 35° C.

It is claimed:

1. A new and distinct *Petunia* plant named 'MIYOPEGB60-1' as illustrated and described.

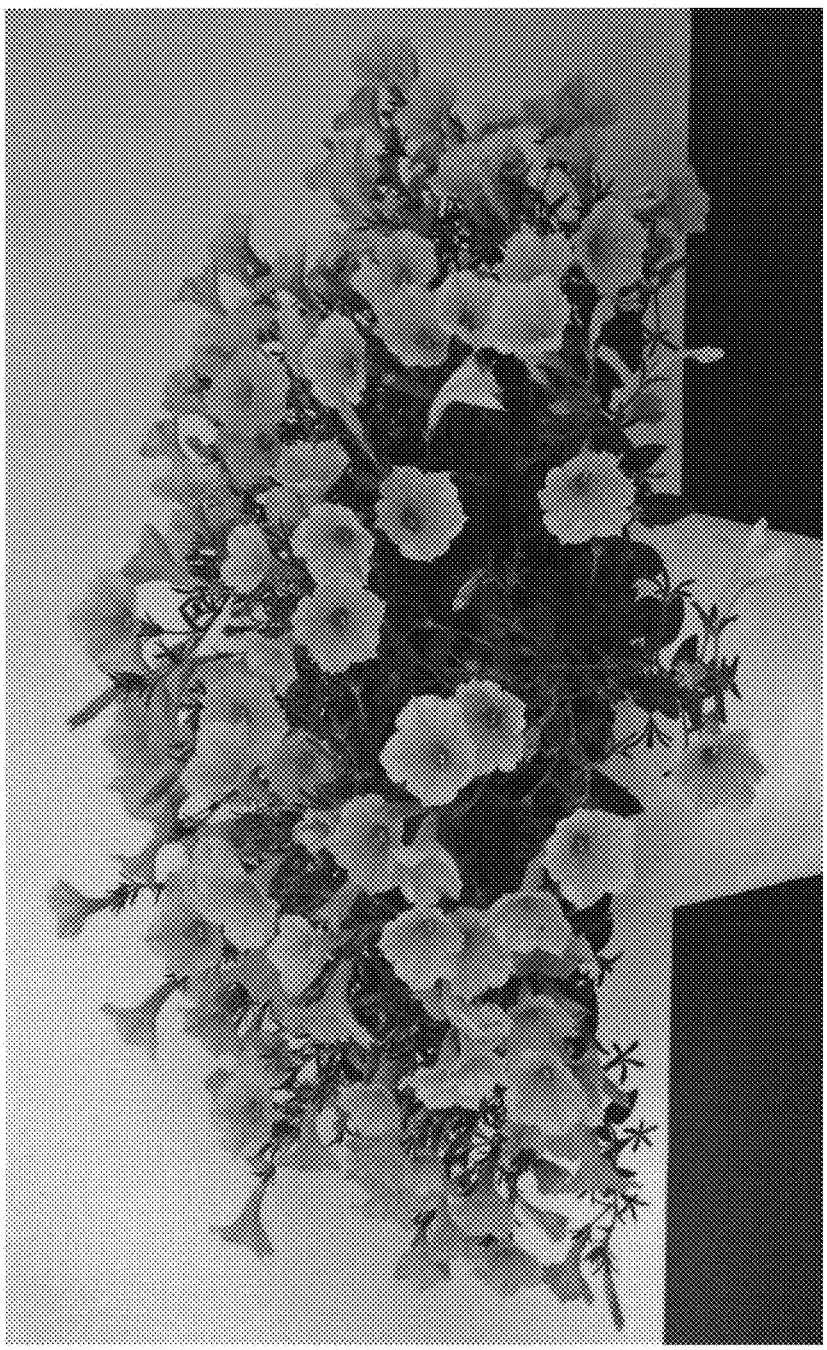

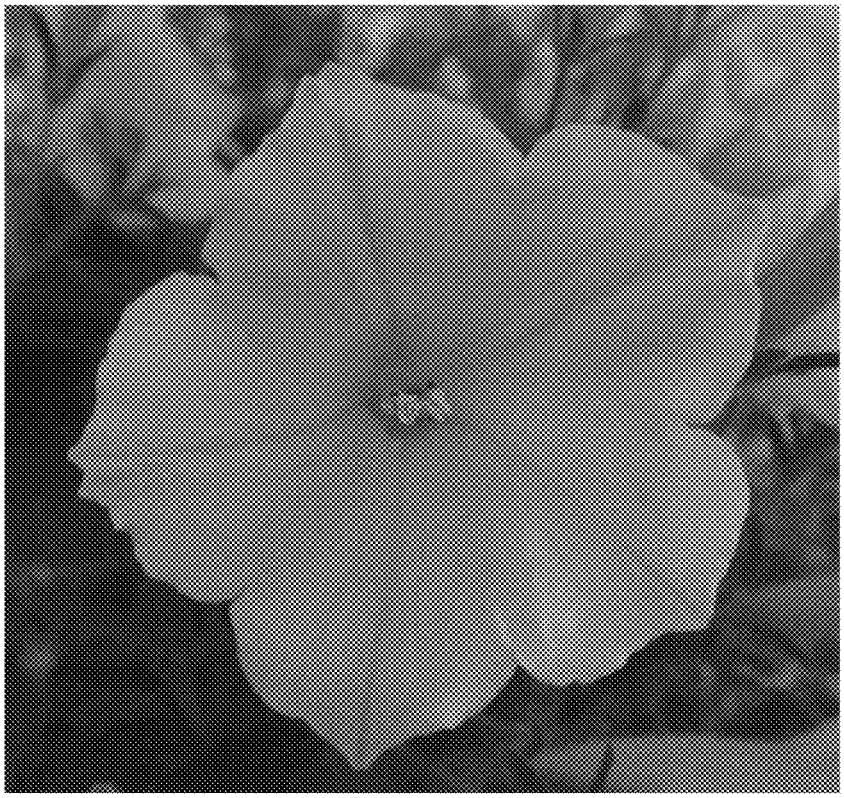

* * * * *